(12) United States Patent
Moriwaki et al.

(10) Patent No.: US 7,691,425 B2
(45) Date of Patent: Apr. 6, 2010

(54) METHOD FOR MANUFACTURING α-GLYCOSYLISOQUERCITRIN, INTERMEDIATE PRODUCT AND BY-PRODUCT THEREOF

(75) Inventors: Masamitsu Moriwaki, Toyonaka (JP); Kazuhiro Emura, Toyonaka (JP); Hisashi Tanaka, Toyonaka (JP)

(73) Assignee: San-Ei Gen F.F.I., Inc., Toyonaka-Shi (JP)

( * ) Notice: Subject to any disclaimer, the term of this patent is extended or adjusted under 35 U.S.C. 154(b) by 1561 days.

(21) Appl. No.: 10/740,607

(22) Filed: Dec. 22, 2003

(65) Prior Publication Data

US 2008/0187622 A1 Aug. 7, 2008

(30) Foreign Application Priority Data

Sep. 29, 2003 (JP) .............................. 2003-338689

(51) Int. Cl.
*A23L 1/00* (2006.01)
(52) U.S. Cl. .............................. 426/52; 426/18; 426/31; 426/541; 426/544
(58) Field of Classification Search ...................... 426/7, 426/18, 31, 49, 52, 541, 544
See application file for complete search history.

(56) References Cited

U.S. PATENT DOCUMENTS

| 5,122,381 | A | 6/1992 | Nishimura et al. | .......... 426/654 |
|---|---|---|---|---|
| 6,420,142 | B1 | 7/2002 | Buchholz et al. | .............. 435/77 |
| 2006/0099690 | A1* | 5/2006 | Chang et al. | .................. 435/75 |

FOREIGN PATENT DOCUMENTS

| EP | 0317033 | | 11/1988 |
|---|---|---|---|
| JP | HI-213293 | | 8/1989 |
| JP | 09025288 | * | 1/1997 |
| JP | 09094077 | * | 4/1997 |
| WO | WO00/26400 | | 5/2000 |
| WO | 2004/027074 | * | 4/2004 |

OTHER PUBLICATIONS

Ellenrieder, G. et al; Thermostabilization of Naringinase from Penicillium Decumbens by Proteins in Solution and Immobilization on Insoluble Proteins; *Biocatalysis and Biotransformation*; 1996; vol. 14, pp. 113-123.
Supplementary European Search Report dated Sep. 5, 2008.

* cited by examiner

*Primary Examiner*—Leslie Wong
(74) *Attorney, Agent, or Firm*—Kratz, Quintos & Hanson, LLP

(57) ABSTRACT

The present invention provides a method for producing isoquercitrin, α-glycosylisoquercitrin, and rhamnose, the method comprising a step of naringin-degrading enzyme treatment during the isoquercitrin production from rutin in the presence of an edible component, such as gelatin, wheat gluten, chitosan, lecithin, a glycerol fatty acid ester, xanthan gum, carrageenan, sodium chondroitin sulfate, casein, enzymatically decomposed gelatin, sodium alginate, konjac extract, gellan gum, guar gum, soybean protein, agar, pectin, yeast extract, egg-white peptide, cluster dextrin, gum arabic, arginine, sodium metaphosphate, karaya gum, locust bean gum, sodium pyrophosphate, glucosamine, chitin, sodium glutamate, dextrin, trehalose, or a grain-based food ingredients. According to the present invention, isoquercitrin and α-glycosylisoquercitrin, which are of use as antioxidants, anti-fading agents, flavor change inhibitors, etc., can be produced in enhanced yields.

12 Claims, No Drawings

METHOD FOR MANUFACTURING α-GLYCOSYLISOQUERCITRIN, INTERMEDIATE PRODUCT AND BY-PRODUCT THEREOF

TECHNICAL FIELD

The present invention relates to a process for producing α-glycosylisoquercitrin and an intermediate product thereof (isoquercitrin), which are widely used as antioxidants, anti-fading agents, flavor change inhibitors, etc., in the fields of food products, fragrances, and cosmetics. α-Glycosylisoquercitrin is a compound prepared by converting isoquercitrin, which is a flavonoid of poor water solubility, to a glycoside of high water solubility. Therefore, isoquercitrin can be considered as an intermediate product in the production of α-glycosylisoquercitrin.

Moreover, the present invention is directed to a method for producing rhamnose generated as a by-product in the production of isoquercitrin.

BACKGROUND OF THE INVENTION

Isoquercitrin, also called isoquercetin, is a compound present in plants such as *Houttuynia cordata, Apocynum venetum* L (yunlong tea), cucumber, cotton, white clover, and mulberry. In addition to antioxidative (anti-fading, flavor change-inhibiting), UV-blocking, and metal chelating actions, this compound is considered to have pharmacological actions such as diuretic, anti-inflammatory, capillary-strengthening, vitamin P-like, and other like actions. Therefore, isoquercitrin is a useful compound that has been used, not only as an anti-fading agent for colored beverages and a flavor change inhibitor for food products, but also as an ingredient for cosmetics and health foods.

For isoquercitrin to exhibit anti-fading or flavor change-inhibiting action, it has to be used in a concentration of at least 0.001 w/v %. However, isoquercitrin dissolves in water at ambient temperature in a concentration of about 0.001 w/v % at most. Therefore, it has been impossible to practically apply isoquercitrin to aqueous products.

To solve this problem, as a method for producing α-glycosylisoquercitrin with high water solubility and the actions derived from isoquercitrin, a method comprising the step of transferring a glucose residue of a substrate to the site of a glucose residue of isoquercitrin using a glycosyltransferase has been previously proposed (Japanese Unexamined Patent Publication No. 213293/1989). α-Glycosylisoquercitrin thus obtained has been widely used as enzyme-treated isoquercitrin in the field of food products, fragrances, cosmetics, quasi-medical products.

α-Glycosylisoquercitrin is produced through a series of reactions such as a generation of isoquercitrin from rutin, and a glycosylation by glycosyltransferase treatment, etc. Enhancing the reaction yield or making the production more efficient is a task that people in the art still have to deal with and improve upon. As a method to accomplish the task, there are a method comprising the step of producing isoquercitrin in the presence of an organic solvent mixture (Japanese Unexamined Patent Publication No. 528133/2002) and a method comprising the step of enhancing reactions by albumin, silk protein, and the like (*Biocatalysis and Biotransformation*, Vol. 14 (1996): 113-123).

DISCLOSURE OF THE INVENTION

An object of the present invention is to provide a process for producing in an enhanced yield α-glycosyl isoquercitrin, which is of use as an antioxidant, anti-fading agent, flavor change inhibitor, etc. Furthermore, another object of the present invention is to provide a process for producing in an enhanced yield isoquercitrin, which is an intermediate product in the production of α-glycosylisoquercitrin, and a process for producing in an enhanced yield rhamnose, which is generated as a by-product during the production of isoquercitrin.

The inventors conducted extensive research to achieve the objectives described above, and found that when rutin is treated with naringinase in the presence of a specific edible component, the reaction proceeds efficiently, thereby producing isoquercitrin and rhamnose in an enhanced yield. As described above, isoquercitrin is an intermediate product in the production of α-glycosylisoquercitrin. The inventors, thus, established, by taking advantage of the above reaction, that α-glycosylisoquercitrin can be efficiently produced as well.

I. The present invention has been accomplished based on the findings described above, and is directed to methods for producing as described hereinbelow isoquercitrin, which is an intermediate product in the production of α-glycosylisoquercitrin:

Item 1. A method for producing isoquercitrin comprising the steps of:

treating rutin with an enzyme having a naringin-degrading activity (hereinafter sometimes referred to as "naringin-degrading enzyme treatment") in the presence of at least one edible component selected from the group consisting of gelatin, wheat gluten, chitosan, lecithin, a glycerol fatty acid ester, xanthan gum, carrageenan, sodium chondroitin sulfate, casein, enzymatically decomposed gelatin, sodium alginate, konjac extract, gellan gum, guar gum, soybean protein, agar, pectin, yeast extract, egg-white peptide, cluster dextrin, gum arabic, arginine, sodium metaphosphate, karaya gum, locust bean gum, sodium pyrophosphate, glucosamine, chitin, sodium glutamate, dextrin, and trehalose; and obtaining an isoquercitrin fraction from the matter treated above.

Item 2. The method for producing isoquercitrin according to Item 1, wherein the glycerol fatty acid ester is at least one member selected from the group consisting of hexaglycerol distearate, tetraglycerol monooleate, tetraglycerol monostearate, decaglycerol monooleate, and decaglycerol stearate.

Item 3. A method for producing isoquercitrin comprising the steps of:

treating rutin with an enzyme having a naringin-degrading activity in the presence of at least one edible component selected from kudzu starch, potato starch, and grain-based food ingredients; and obtaining an isoquercitrin fraction from the matter treated above.

Item 4. The method for producing isoquercitrin according to Item 3, wherein the grain-based food ingredients are food ingredients made from grain selected from the group consisting of rice, barley, wheat, rye, triticale, oat, corn, barnyard millet, foxtail millet, sorghum, millet, Job's-tears, legumes, and buckwheat.

Item 5. The method for producing isoquercitrin according to Item 3, wherein the grain-based food ingredient is food ingredient made from wheat selected from the group consisting of wheat protein, wheat flour, wheat bran, and wheat germ.

II. Moreover, the present invention relates to methods for producing α-glycosylisoquercitrin, which is useful as a flavonoid with high water solubility:

Item 6. A method for producing α-glycosylisoquercitrin as represented by Formula (1) below:

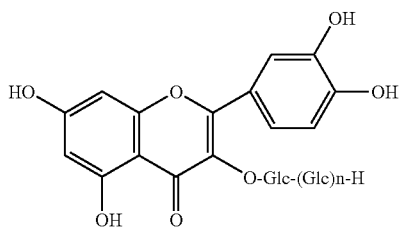

wherein "Glc" refers to a glucose residue, and n represents an integer of 1 or more, the method comprising treating isoquercitrin obtained the process recited in any of Items 1 to 5 with a glycosyltransferase.

Item 7. The method for producing α-glycosylisoquercitrin according to Item 6, wherein n in Formula (1) is an integer of 1 to 7.

III. As described above, by treating rutin with a naringin-degrading enzyme, rhamnose is generated during the production of the aforementioned isoquercitrin. Therefore, the present invention also relates to methods for producing rhamnose, which is generated as a by-product in the isoquercitrin production:

Item 8. A method for producing rhamnose comprising the steps of:

treating rutin with an enzyme having a naringin-degrading activity in the presence of at least one edible component selected from the group consisting of gelatin, wheat gluten, chitosan, lecithin, a glycerol fatty acid ester, xanthan gum, carrageenan, sodium chondroitin sulfate, casein, enzymatically decomposed gelatin, sodium alginate, konjac extract, gellan gum, guar gum, soybean protein, agar, pectin, yeast extract, egg-white peptide, cluster dextrin, gum arabic, arginine, sodium metaphosphate, karaya gum, locust bean gum, sodium pyrophosphate, glucosamine, chitin, sodium glutamate, dextrin, and trehalose; and obtaining a rhamnose fraction from the matter treated above.

Item 9. The method for producing rhamnose according to Item 8, wherein the glycerol fatty acid ester is at least one member selected from the group consisting of hexaglycerol distearate, tetraglycerol monooleate, tetraglycerol monostearate, decaglycerol monooleate, and decaglycerol stearate.

Item 10. A method for producing rhamnose comprising the steps of:

treating rutin with an enzyme having a naringin-degrading activity in the presence of at least one edible component selected from kudzu starch, potato starch, and grain-based food ingredients; and obtaining a rhamnose fraction from the matter treated above.

Item 11. The method for producing rhamnose according to Item 10, wherein the grain-based food ingredients are food ingredients made from grains selected from the group consisting of rice, barley, wheat, rye, triticale, oat, corn, barnyard millet, foxtail millet, sorghum, millet, Job's-tears, legumes, and buckwheat.

Item 12. A method for producing rhamnose according to Item 10, wherein the grain-based food ingredients are food ingredients made from wheat, selected from the group consisting of wheat protein, wheat flour, wheat bran, and wheat germ.

IV. Furthermore, the present invention relates to the formulations described below:

Item 13. An isoquercitrin formulation comprising as an active ingredient isoquercitrin obtained according to a method recited in any of Items 1 to 5.

Item 14. An α-glycosylisoquercitrin formulation comprising as an active ingredient α-glycosylisoquercitrin obtained according to a process recited in Item 6 or 7.

As shown in the reaction scheme below, isoquercitrin (b), rhamnose (c), and α-glycosylisoquercitrin (d) can be produced and obtained by a series of reactions using rutin (a) as a starting material, and are useful compounds that have been widely used in the fields of food products, fragrances, cosmetics, etc. In the reaction scheme below, "Glc" refers to a glucose residue; "Rha" refers to a rhamnose residue; and n represents an integer of 1 or more.

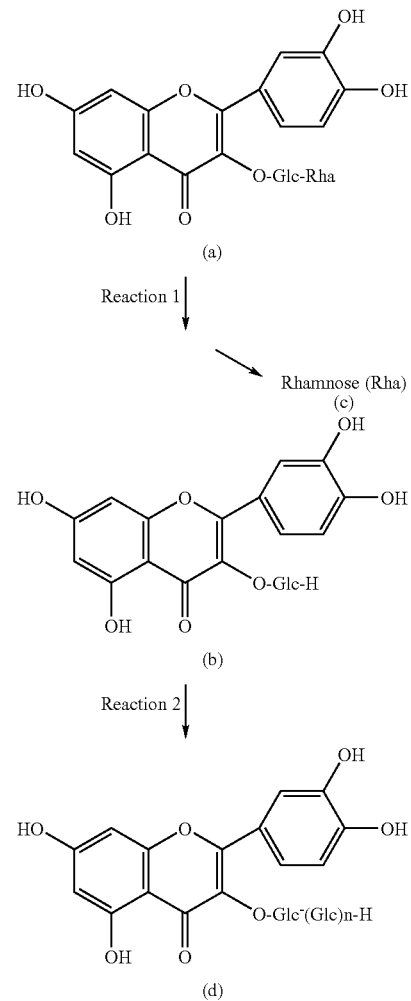

Hereinbelow, the present invention is described in more detail with reference to this reaction scheme.

BEST MODE FOR CARRYING OUT THE INVENTION (I) Method for Producing Isoquercitrin, and Isoquercitrin Formulation As shown in Reaction 1 of the above scheme, when rutin (a) is reacted with an enzyme having a naringin-degrading activity (hereinafter sometimes referred to as a "naringin-degrading enzyme"), the rhamnose residue is cleaved from the rutin, producing isoquercitrin (b). The present invention relates to a method for producing isoquercitrin comprising conducting the naringin-degrading enzyme treatment of Reaction 1 in the presence of a specific edible component.

Enzymes having a naringin-degrading activity (naringin-degrading enzymes) herein include, no matter how termed, all enzymes that exhibit an activity of decomposing rutin into isoquercitrin and rhamnose. Naringinase can be named as a typical example having such an activity. Also, it is known that enzymes having such a naringin-degrading activity can be found among rhamnosidase ($\alpha$-L-rhamnosidase: EC.3.2.1.40), hesperidinase, pectinase, etc. Such enzymes are commercially available. For example, naringinase is available from Amano Enzyme, Inc. (Japan, trade name: naringinase "Amano"), and Tanabe Seiyaku Co., Ltd., (Japan).

These enzymes need not be purified, and insofar as the object of the invention can be achieved, can be in a crude form. For example, it is known that naringinase is produced by microorganisms (naringinase-producing microorganisms) belonging to *Aspergillus niger, Penicillium*, etc. Therefore, isoquercitrin can be prepared by inoculating such a naringinase-producing microorganism into a rutin-supplemented medium and performing the reaction by fermentation. Alternatively, isoquercitrin can be prepared by reacting rutin with an immobilizing naringinase or naringinase-producing microorganisms in a batch-wise or continuous manner.

Examples of specific edible components usable herein include gelatin, wheat gluten, chitosan, xanthan gum, carrageenan, sodium chondroitin sulfate, enzymatically decomposed gelatin, sodium alginate, konjac extract, gellan gum, guar gum, agar, pectin, cluster dextrin, gum arabic, karaya gum, locust bean gum, glucosamine, chitin, dextrin, and like thickeners; lecithin, glycerol fatty acid esters (for example, hexaglycerol distearate, tetraglycerol monostearate, tetraglycerol monooleate, decaglycerol monooleate, decaglycerol stearate, etc), and like emulsifiers; casein, soybean protein, egg-white peptide, and like animal or vegetable proteins; arginine, sodium glutamate, and like amino acids; sodium metaphosphate, sodium pyrophosphate, and like inorganic salts (chelating agents); yeast extracts; trehalose; kudzu starch, potato starch, and like vegetable starches; and various other food ingredients made from grains (grain-based food ingredients). Among these, preferable are gelatin, wheat gluten, chitosan, lecithin, glycerol fatty acid esters (for example, hexaglycerol distearate, tetraglycerol monostearate, decaglycerol stearate, etc.), xanthan gum, carrageenan, sodium chondroitin sulfate, casein, enzymatically decomposed gelatin, sodium alginate, konjac extract, gellan gum, guar gum, soybean protein, agar, and various grain-based food ingredients. Particularly preferable are gelatin, glycerol fatty acid esters (for example, hexaglycerin distearic acid ester, tetraglycerin monostearic acid ester, decaglycerin stearic acid ester, etc.), xanthan gum, carrageenan, sodium chondroitin sulfate, casein, enzymatically decomposed gelatin, sodium alginate, konjac extract, and various grain-based food ingredients. Especially particularly preferable are gelatin, wheat gluten, chitosan, lecithin, decaglycerol stearate, xanthan gum, carrageenan, sodium chondroitin sulfate, and various grain-based food ingredients. Yet more particularly preferable are gelatin, wheat gluten, chitosan, lecithin, and various grain-based food ingredients. Among the aforementioned glycerol fatty acid esters, preferable are those that have an HLB of 8 to 11.

Grains as used herein refer to edible nuts or seeds of poaceous crops (cereals), papilionaceous crops (legumes and pulses), and buckwheat. Examples of edible nuts or seeds of poaceous crops (cereals) include rice, wheat (common wheat, durum wheat), barley (including naked barley), rye, triticale, oat, corn, barnyard millet, foxtail millet, sorghum, millet, and Job's-tears. Examples of edible nuts or seeds of papilionaceous crops (legumes and pulses) include soybean, adzuki bean, mung bean, cowpea, chickpea, lentil, and like legumes.

The present invention is not limited to these grains being used as edible components as they are, and they are usually used in the form or composition of general food ingredients after ordinary food processing.

Examples of such food ingredients include rice flour, rice protein, rice bran, rice starch, whole grain, and like various food ingredients made from rice; wheat flour (strong flour, semi-strong flour, medium flour, soft flour), wheat starch, wheat protein (wheat gluten, wheat glutenin, wheat glutelin), wheat germ (including defatted germ), wheat bran, whole grain, and like various food ingredients made from wheat; barley flour, whole grain and like various food ingredients made from barley; rye flour, whole grain and like various food ingredients made from rye; oat flour, whole grain and like various food ingredients made from oat; corn flour, corn starch, corn grits, corn gluten, and like various food ingredients made from corn; various food ingredients made from barnyard millet; various food ingredients made from foxtail millet; various food ingredients made from sorghum; various food ingredients made from millet; various food ingredients made from Job's-tears; soybean flour, soybean protein, soybean lecithin, soybean casein, and various like food ingredients made from soybean; various food ingredients made from adzuki bean; and buckwheat flour, whole grain, and various food ingredients made from buckwheat.

These food ingredients, when used as edible components in the present invention, may be processed (ground, extracted, roasted, etc.) as necessary insofar as the effect of the invention is not impaired. Among the food ingredients made from such grains, preferable are wheat proteins (wheat gluten, wheat glutenin, wheat glutelin), soybean proteins, and like vegetable proteins; and wheat flours (strong flour, semi-strong flour, medium flour, soft flour). Especially preferable are wheat proteins.

These edible components can be used alone or as a combination of two or more types.

Conditions of reaction using the naringin-degrading enzyme are not limited insofar as the naringin-degrading enzyme can exhibit a naringin-degrading activity in an aqueous mixture containing rutin, the naringin-degrading enzyme, and the aforementioned edible component. For example, when a naringin-degrading enzyme with an enzyme-specific activity of about 100 units (1 unit equals the enzyme level that can produce in 30 minutes in a normal naringin solution (pH 3.5) a reducing sugar corresponding to 1 mg of rhamnose) is used, the amount of naringin-degrading enzyme per part by weight of rutin can be suitably selected from the range of 0.01 to 5 parts by weight, preferably 0.02 to 3 parts by weight, and more preferably 0.05 to 2 parts by weight.

The amount of edible component to be used varies depending of the type of edible component and cannot be specified. However, it can be suitably selected from the range of, for example, 0.001 to 20 parts by weight, preferably 0.002 to 10 parts by weight, and more preferably 0.005 to 5 parts by weight, per part by weight of rutin.

Although the amount of rutin in the reaction mixture is not limited, it is usually desirable, in view of more efficient isoquercitrin production, for the reaction mixture (100 wt. %) to have rutin in a proportion of 0.1 to 20 wt. %, preferably 0.1 to 15 wt. %, and more preferably 0.1 to 10 wt. %.

Temperature and pH conditions of the reaction mixture vary according to the type of naringin-degrading enzyme to be used. For example, naringinase "Amano" manufactured by Amano Enzyme, Inc., or similar naringinase is used, the temperature is preferably lower than 75° C. Within this temperature range, it is industrially advantageous to select a temperature from about 40 to about 75° C., and preferably from about 60 to about 75° C. The pH condition is usually 8 or lower, preferably 4 to 6.

The reaction proceeds with remaining stationary, stirring or shaking can be applied. To prevent oxidation during the reaction, air present in the headspace of the reaction container can be replaced by an inert gas, such as nitrogen or the like. It is also possible to add an antioxidant, such as ascorbic acid or the like, to the reaction mixture.

In this manner, the rhamnose residue is cleaved from rutin, thereby yielding the desired isoquercitrin as well as rhamnose.

If desired, it is possible to isolate isoquercitrin from the reaction mixture and purify it. For example, isoquercitrin, which is poorly water soluble, can be isolated by precipitation by cooling the reaction mixture to 40° C. or lower. Isoquercitrin can be purified according to conventional method(s) without limitation. Specific examples include various resin treatments (absorption, ion exchange, gel filtration, etc.), membrane treatments (ultrafiltration membrane, reverse osmotic membrane, ion-exchange membrane, ζ(zeta)-potential membrane, etc.), electrodialysis, solvent fractionation, activated carbon treatment, etc.

Isoquercitrin thus obtained can be used not only as an antioxidant, anti-fading agent, flavor change inhibitor and the like in the fields of food products, fragrances, and cosmetics, but also as a starting material in the production of α-glycosylisoquercitrin described hereinafter (when rutin is used as a starting material, isoquercitrin can be regarded as an intermediate product in the production of α-glycosylisoquercitrin). When isoquercitrin is used as a starting material or an intermediate product in the production of α-glycosylisoquercitrin, it need not be purified and can be in a crude form (for example, a precipitate as described above) or in a form of a reaction mixture as above.

When isoquercitrin is to be used as is as an antioxidant, anti-fading agent, flavor change inhibitor, or the like, the isoquercitrin isolated and purified as above may be further mixed with diluents, carriers, additives, or similar components and prepared into desired formulations according to the usual formulation techniques.

Diluents and carries usable herein are not limited insofar as the effect of the invention is not impaired. Examples thereof include sucrose, glucose, fructose, maltose, trehalose, lactose, oligosaccharide, dextrin, dextran, cyclodextrin, starch, starch syrup, isomerized liquid sugar, and like saccharides; ethanol, propylene glycol, glycerol, and like alcohols; sorbitol, mannitol, erythritol, lactitol, xylitol, maltitol, reduced palatinose, reduced amylolysis products, and like sugar alcohols; triacetin and like solvents; gum arabic, carrageenan, xanthan gum, guar gum, gellan gum, pectin, and like polysaccharides; and water. Examples of additives include chelating agents and like auxiliaries, flavorings, spice extracts, antiseptic agents, etc.

For example, when an antioxidant is prepared in the form of a liquid formulation containing isoquercitrin along with such diluents, carriers, or additives, it is desirable in view of usability that isoquercitrin is contained in a proportion of 0.01 to 50 wt. %, and preferably 0.1 to 30 wt. %, based on 100 wt. % of the formulation.

The formulation of present invention is not limited in form, and can be prepared in any desired form, such as powders, granules, tablets, or like solid forms; solutions, emulsions, or like liquid forms; pastes or like semi-solid forms; etc.

(II) Method for Producing α-Glycosylisoquercitrin, and α-Glycosylisoquercitrin Formulation In Reaction 2 shown the above reaction scheme, when isoquercitrin (b) obtained according to the aforementioned process is treated with a glucosyltransferase, at least one glucosyl group is added to the glucosyl residue of isoquercitrin (b), thereby forming an α-glycosylisoquercitrin (c). The present invention relates to a method for producing α-glycosylisoquercitrin comprising using as a starting material in Reaction 2 isoquercitrin (b) obtained by Reaction 1.

The purity of isoquercitrin (b) used as a starting material in Reaction 2 is not limited insofar as isoquercitrin (b) is obtained according to the process described in (I) above. When Reaction 2 is conducted successive to Reaction 1, for example, the reaction mixture obtained by Reaction 1 is cooled to 40° C. or lower to precipitate isoquercitrin, and the resultant isoquercitrin is recovered and used in Reaction 2.

Methods for producing α-glycosylisoquercitrin (c) from isoquercitrin (b) are not restricted. Therefore, methods that have been known or that may become known in the future can be employed. Usually, α-glycosylisoquercitrin is produced by transferring an equimolar or greater amount of glucose residues to isoquercitrin (b) to make a glycoside (hereinafter referred to as glycosidation) using glucosidase, transglucosidase, or like glucosyltransferases.

Glucose sources used in the glycosidation are such that at least one glucose residue thereof can be transferred to one molecule of isoquercitrin (b). Examples are glucose itself, maltose, amylose, amylopectin, starch, liquefied starch, saccharified starch, dextrin, cyclodextrin, etc. The amount of glucose source used is usually 0.1 to 20 parts by weight, preferably 0.5 to 15 parts by weight, and more preferably 1 to 10 parts by weight, per part by weight of isoquercitrin (b) present in the reaction mixture.

Examples of usable glucosidases are α-amylase (E.C.3.2.1.1), α-glucosidase (E.C.3.2.1.20), β-amylase (E.C.3.2.1.2), glucoamylase (E.C.3.2.1.3), etc. Examples of usable transglucosidases are cyclodextrin glucanotransferase (E.C.2.4.1.19) (hereinafter referred to as CGTase) and similar transglucosidases.

It is known that CGTase is produced by bacteria belonging to the genus *Bacillus*, such as *Bacillus circulans, Bacillus macerans, Bacillus stearothermophilus, Bacillus megaterium, Bacillus polymyxa*, etc., and the genus *Klebsiella*, such as *Klebsiella pneumoniae* and the like. CGTase produced by any of these bacteria can be used in the present invention without limitation.

The glucosyltransferases described above are readily available enzymes. For convenience, commercially available enzymes (such as that manufactured by Amano Enzyme, Inc., trade name: CONTIZYME, Japan) can be used. These enzymes need not be purified, and insofar as the object of the invention can be achieved, may be in a crude form. For example, α-glycosylisoquercitrin can be prepared by inoculating a glucosyltransferase-producing microorganism into an isoquercitrin-supplemented medium and performing the reaction by fermentation.

Alternatively, α-glycosylisoquercitrin can also be prepared by reacting isoquercitrin (b) with an immobilizing glucosyltransferase or glucosyltransferase-producing microorganism in a batch-wise or continuous manner.

Conditions of reaction using the glucosyltransferase are not limited insofar as the glucosyltransferase can function in an aqueous mixture containing isoquercitrin (b), the glucosyltransferase, and the aforementioned glucose source. When the glucosyltransferase is, for example, CGTase having an enzyme-specific activity of about 100 units (1 unit equals the enzyme level that can produce in 1 minute 1 mg of β-cyclodextrin from soluble starch), the amount of glucosyltransferase used per part by weight of isoquercitrin (b) can be suitably selected from the range of 0.001 to 20 parts by weight, preferably about 0.005 to about 10 parts by weight, and more preferably about 0.01 to about 5 parts by weight.

Although the amount of isoquercitrin (b) in the reaction mixture is not limited, it is usually desirable, in view of efficient glycosidation, for the reaction mixture (100 wt. %) to have isoquercitrin (b) in a proportion of 0.1 to 30 wt. %, preferably 0.5 to 20 wt. %, and more preferably 1 to 10 wt. %.

The temperature of the reaction mixture varies according to the type of enzyme used, but can be suitably selected from the range of about 80° C. or lower. Within this temperature range, it is industrially advantageous to select a temperature from about 20 to about 80° C., and preferably from about 40 to about 75° C. The pH condition is usually about 3 to about 11, and preferably about 4 to about 8.

The reaction proceeds with remaining stationary, stirring or shaking can be applied. To prevent oxidation during the reaction, air present in the headspace of the reaction container can be replaced by an inert gas, such as nitrogen or the like. It is also possible to add an antioxidant, such as ascorbic acid or the like, to the reaction mixture.

With respect to the glucosyltransferases, glucosidases and transglucosidases can be used alone or in combination (simultaneously or successively).

In this manner, a glucose group is added to the glucose residue of isoquercitrin, thereby yielding a desired α-glycosylisoquercitrin.

The number of glucose groups added to the glucose residue of isoquercitrin (the number represented by "n" in Formula (1)) is not limited, and it is usually selected from 1 to 30, preferably 1 to 12, and more preferably 1 to 7. The number of glucose groups added ("n") can be suitably modified. For example, it is possible to obtain α-glycosylisoquercitrin having a desired number of glucose residue by, once an α-glycosyl isoquercitrin is produced, treating it with a single amylase or a combination of various amylases (α-amylase, β-amylase, glucoamylase, α-glucosidase, maltase, etc.) to reduce the number of glucose linkages in the α-glycosyl isoquercitrin produced by Reaction 2 (reaction scheme).

If desired, it is possible to isolate α-glycosylisoquercitrin from the reaction mixture of Reaction 2 (reaction scheme) or the reaction mixture of the aforementioned amylase treatment, and purify it. For example, α-glycosylisoquercitrin can be isolated by precipitation by acidifying and cooling the reaction mixture. α-Glycosylisoquercitrin can be purified according to conventional method(s) without limitation. Specific examples include various resin treatments (absorption, ion exchange, gel filtration, etc.), membrane treatments (ultrafiltration membrane, reverse osmotic membrane, ion-exchange membrane, ζ(zeta)-potential membrane, etc.), electrodialysis, salt-induced precipitation, acid-induced precipitation, recrystallization, solvent fractionation, activated carbon treatment, etc.

α-Glycosylisoquercitrin thus obtained is a highly water soluble flavonol glycoside wherein the glucose residue of isoquercitrin (quercetin-3-O-monoglycoside) has further an equimolar or greater amount of glucose groups. Therefore, it can effectively demonstrate the remarkable properties derived from isoquercitrin (for example, antioxidative, antifading, and flavor change inhibiting actions) in aqueous solvents. α-Glycosylisoquercitrin can thus be used as a water-soluble antioxidant, anti-fading agent, flavor change inhibitor, etc., in the fields of food products, fragrances, and cosmetics.

When α-glycosylisoquercitrin is to be used as an antioxidant, anti-fading agent, flavor change inhibitor, or the like, the α-glycosylisoquercitrin isolated and purified as above may be further mixed with diluents, carriers, additives, or similar components and prepared into desired formulations according to the usual formulation techniques.

Diluents and carries usable herein are not limited insofar as the effect of the invention is not impaired. Examples thereof include sucrose, glucose, fructose, maltose, trehalose, lactose, oligosaccharide, dextrin, dextran, cyclodextrin, starch, starch syrup, isomerized liquid sugar, and like saccharides; ethanol, propylene glycol, glycerol, and like alcohols; sorbitol, mannitol, erythritol, lactitol, xylitol, maltitol, reduced palatinose, reduced amylolysis products, and like sugar alcohols; triacetin and like solvents; gum arabic, carrageenan, xanthan gum, guar gum, gellan gum, pectin, and like polysaccharides; and water. Examples of additives include chelating agents and like auxiliaries, flavorings, spice extracts, antiseptic agents, etc.

When the formulations are prepared using α-glycosylisoquercitrin along with above-mentioned diluents, carriers, or additives, it is desirable in view of usability that α-glycosylisoquercitrin is contained in a proportion of 0.01 to less than 100 wt. %, and preferably 1 to less than 100 wt. %, based on 100 wt. % of formulation.

The formulation of present invention is not limited in form, and can be prepared in any desired form, such as powders, granules, tablets, or like solid forms; solutions, emulsions, or like liquid forms; pastes or like semi-solid forms; etc.

(III) Method for Producing Rhamnose, and Rhamnose Formulation

In Reaction 1 shown above, when rutin (a) is reacted with an enzyme having a naringin-degrading activity, rhamnose is produced as well as isoquercitrin (b). Therefore, the present invention is also directed to methods for producing rhamnose comprising conducting in Reaction 1 the naringin-degrading enzyme treatment in the presence of a specific edible component.

The production of rhamnose can be performed according to the process of Reaction 1 described in (I) above using rutin (a) as a starting material. Due to the naringin-degrading enzyme treatment, the reaction mixture containing rhamnose (the mixture containing isoquercitrin, rhamnose, and unreacted rutin) is obtained. It is possible to isolate rhamnose from the mixture and purify it as necessary.

For example, isoquercitrin, which is poorly water soluble, is precipitated by cooling the reaction mixture to 40° C. or lower, and removed by centrifugal separation, filtration, or like conventional techniques of solid-liquid separation. Rhamnose can be recovered from the liquid phase thus obtained.

Rhamnose thus recovered may be further subjected to a purification treatment. Rhamnose can be purified according to conventional purification method(s) without limitation. Specific examples include various resin treatments (absorption, ion exchange, gel filtration, etc.), membrane treatments (ultrafiltration membrane, reverse osmotic membrane, ion-exchange membrane, ζ(zeta)-potential membrane, etc.), electrodialysis, solvent fractionation, activated carbon treatment, etc.

Rhamnose thus obtained can be used, for example, as a sugar source, sweetener, food additive, and pharmaceutical additive in the fields of food products, pharmaceuticals, quasi-medical products, fragrances, and cosmetics. Furthermore, it can be used as an ingredient in the production of flavorings such as furaneol and the like, and, moreover, it can preferably be used as an ingredient in the production of pharmaceuticals, cosmetics, and other chemical substances.

According to the present invention, isoquercitrin, which is an intermediate product in the production of α-glycosylisoquercitrin, can be produced in an enhanced yield. Therefore, the present invention is not only of use as a method for efficiently producing isoquercitrin, but also of use for efficiently producing α-glycosylisoquercitrin. Furthermore, as isoquercitrin is produced from rutin, rhamnose is generated. Therefore, from a different perspective, the present invention, which is directed to a method for producing isoquercitrin, is also useful as a method for producing rhamnose that is a sugar source from rutin in an enhanced yield.

EXAMPLES

Experimental Examples and Examples are given below to illustrate the invention in more detail, but the scope of the invention is not limited to these examples.

Experimental Example 1

Rutin (5 g) was dispersed in about 90 ml of water. One of the various edible components (food additives) listed in Table 1 was added thereto in a proportion of 0.05 wt. % or 0.5 wt. %, and dissolved or dispersed. The mixture was heated to 72° C. The pH thereof was adjusted to 4.7 by pH adjustors (sulfuric acid, sodium hydroxide). Water was added to the mixture to a total volume of 100 ml. The reaction was initiated by introducing 1 ml of an aqueous solution of naringinase (manufactured by Amano Enzyme, Inc., trade name: naringinase "Amano") prepared by mixing 0.02 g of naringinase (specific activity: 3000 U/g) with 10 ml of water. Five hours later, 4 μl of the reaction solution was sampled and dissolved in 50 μl N sodium hydroxide. A mixed solution of 15 volume % acetonitrile and 0.085 w/v % phosphoric acid was added (2 ml in total) thereto to stop the reaction. The reaction solution thus obtained was subjected to HPLC under the conditions described below. The amount of isoquercitrin produced was calculated based on the ratio of the peak area for isoquercitrin relative to the sum of the peak areas for rutin and isoquercitrin. The yield (%) of isoquercitrin was calculated from the amount of isoquercitrin. As a control experiment, a similar reaction was conducted in a system in which none of the edible components was present, and the isoquercitrin yield (%) was obtained in the same manner.

<HPLC Conditions>

Column: ODS column (Tosoh Corporation, Super ODS, φ4.6×100 mm, Japan)

Mobile Phase Mixed solution of 15 volume % acetonitrile and 0.085 w/v % phosphoric acid Flow Rate: 0.8 ml/min Detection: UV 350 nm Column Temperature: 40° C.

The results are also shown in Table 1.

TABLE 1

| Food additive | Trade name | Make | Form | Concentration (%) | Yield (%) |
|---|---|---|---|---|---|
| Control | | | | | 16.34 |
| Chitin | Reagent | Seikagaku Corporation | Powdery | 0.5 | 37.45 |
| Sodium glutamate | Gluace S-2 | Kyowa Hakko Kogyo Co., Ltd. | Powdery | 0.5 | 31.13 |
| Dextrin | Sandex # 70 | Sanwa Cornstarch Co., Ltd. | Powdery | 0.5 | 30.07 |
| Trehalose | Reagent | Tokyo Kasei Kogyo Co., Ltd. | Powdery | 0.5 | 20.64 |
| Gelatin | Gelatin E-170 | Jellice Co. Ltd | Granular | 0.05 | 59.9 |
| Wheat gluten | Ema-Soft M-1000 | Riken Vitamin Co., Ltd. | Powdery | 0.05 | 59.66 |
| Gelatin | Gelatin E-200 | Jellice Co. Ltd | Granular | 0.05 | 59.47 |
| Gelatin | Gelatin E-120 | Jellice Co. Ltd | Granular | 0.05 | 58.51 |
| Gelatin | Gelatin E-260 | Jellice Co. Ltd | Granular | 0.05 | 58.23 |
| Chicken gelatin (acid gelatin) | Chicken Gelatin | Nippon Meat Packers Inc. | Granular | 0.05 | 58 |
| Gelatin | Gelatin E-140 | Jellice Co. Ltd | Granular | 0.05 | 57.94 |
| Beef gelatin (alkali gelatin) | Gelatin GLS-A | Nippi Inc. | Powdery | 0.05 | 57.73 |
| Pork gelatin (alkali gelatin) | Gelatin F-3284 | Jellice Co. Ltd | Powdery | 0.05 | 57.29 |
| Chitosan | Chitosan | Kimika Corp. | Powdery | 0.05 | 56.77 |
| Lecithin | Basis LP-20B | Nisshin Oillio Ltd. | Powdery | 0.05 | 52.15 |
| Decaglycerol stearate | Ryoto Polygly Ester S-28D | Mitsubishi-Kagaku Foods Corp. | Flaky | 0.05 | 44.29 |
| Xanthan gum | Bistop D-3000 | San-Ei Gen F.F.I. Inc. | Powdery | 0.05 | 43.11 |
| Carrageenan | Carrageenan CS-56 | San-Ei Gen F.F.I. Inc. | Powdery | 0.05 | 40.68 |
| Sodium chondroitin sulfate | Chondroitin Sulfate Sodium SG | San-Ei Gen F.F.I. Inc. | Powdery | 0.05 | 39.2 |
| Hexaglycerol distearate | SY-Glyster SS-5S | Sakamoto Yakuhin Kogyo Co., Ltd. | Flaky | 0.05 | 38.36 |
| Casein (milk-derived) | Reagent | Kishida Chemical Co., Ltd | Powdery | 0.05 | 36.01 |
| Enzymatically decomposed gelatin | Water-Soluble Collagen Peptide PA | Kyowa Hakko Kogyo Co., Ltd. | Powdery | 0.05 | 34.68 |
| Sodium alginate | Kimitsu Algin | Kimika Corp. | Powdery | 0.05 | 34.26 |
| Konjac extract | Rheolex RS | Shimizu Chemical Corp. | Powdery | 0.05 | 33.41 |
| Decaglycerol tristearate | SY-Glyster TS-7S | Sakamoto Yakuhin Kogyo Co., Ltd. | Flaky | 0.05 | 31.91 |
| Tetraglycerol monostearate | SY-Glyster MS-3S | Sakamoto Yakuhin Kogyo Co., Ltd. | Flaky | 0.05 | 29.89 |
| Tetraglycerin monostearate | SY-Glyster MO-3S | Sakamoto Yakuhin Kogyo Co., Ltd. | Liquid | 0.05 | 28.17 |
| Gellan gum | Kelcogel | San-Ei Gen F.F.I. Inc. | Powdery | 0.05 | 26.76 |

TABLE 1-continued

| Food additive | Trade name | Make | Form | Concentration (%) | Yield (%) |
|---|---|---|---|---|---|
| Guar gum | Procol GF | Somar Corp. | Powdery | 0.05 | 26.26 |
| Soybean protein | Fujipro E | Fuji Oil Co., Ltd. | Powdery | 0.05 | 25.97 |
| Agar | Ultra Agar | Ina Food Industry Co., Ltd. | Powdery | 0.05 | 25.8 |
| Pectin | GENU Pectin Type VIS | CP Kelco | Powdery | 0.05 | 24.22 |
| Yeast extract | Meastpowder P21 | Asahi Food & Healthcare, Ltd. | Powdery | 0.05 | 23.84 |
| Egg-white peptide | Egg-white Peptide EP-1 | Q.P. Corporation | Powdery | 0.05 | 23.58 |
| Cluster dextrin | Cluster Dextrin | Ezaki Glico Co., Ltd. | Powdery | 0.05 | 23.41 |
| Gum arabic | Powdered Gum Arabic HP | Sanei Yakuhin Boeki Co., Ltd. | Powdery | 0.05 | 23.34 |
| Arginine | L-Arginine Kyowa | Kyowa Hakko Kogyo Co., Ltd. | Powdery | 0.05 | 22.86 |
| Sodium metaphosphate | Ultrapolin | Taihei Chemical Industrial Co., Ltd. | Powdery | 0.05 | 22.3 |
| Karaya gum | Pasteurize Karayacol | Sanei Yakuhin Boeki Co., Ltd. | Powdery | 0.05 | 22.08 |
| Decaglycerol monooleate | SY-Glyster MO-7S | Sakamoto Yakushin Kogyo Co., Ltd. | Liquid | 0.05 | 21.82 |
| Locust bean gum | Locust Bean Gum F | San-Ei Gen F.F.I. Inc. | Powdery | 0.05 | 21.1 |
| Sodium pyrophosphate | Crystalline Tetrasodium Pyrophosphate | Taihei Chemical Industrial Co., Ltd. | Powdery | 0.05 | 20.64 |
| Glucosamine | Glucosamine A | San-Ei Gen F.F.I. Inc. | Powdery | 0.05 | 20.4 |

The results show that treating rutin with naringinase in the presence of any of the edible components listed above increases the amount of isoquercitrin produced (yield).

Experimental Example 2

This experiment was conducted in the same manner as in Experimental Example 1 except that the food ingredients listed in Table 2 were used as edible components. The amount of isoquercitrin produced was calculated based on HPLC analysis, and the yield (%) thereof was obtained accordingly. The results are also shown in Table 2.

TABLE 2

| Food ingredients | Form | Concentration (%) | Yield (%) |
|---|---|---|---|
| Control | | | 16.34 |
| Flour (soft flour) | Powdery | 0.5 | 56.1 |
| Flour (strong flour) | Powdery | 0.5 | 55.42 |
| Rye | Powdery | 0.5 | 55.07 |
| Triticale | Powdery | 0.5 | 51.8 |
| Rice bran | Powdery | 0.5 | 50.4 |
| Wheat germ | Powdery | 0.5 | 49.11 |
| Soybean | Powdery | 0.5 | 47.81 |
| Wheat bran | Powdery | 0.5 | 46.75 |
| Adzuki bean | Powdery | 0.5 | 46.27 |
| Barley | Powdery | 0.5 | 45.52 |
| Buckwheat | Powdery | 0.5 | 43.4 |
| Foxtail millet | Powdery | 0.5 | 43.9 |
| Millet | Powdery | 0.5 | 41.8 |
| Job's-tears | Powdery | 0.5 | 35.17 |
| Barnyard millet | Powdery | 0.5 | 33.05 |
| Corn starch | Powdery | 0.5 | 42.2 |
| Potato starch | Powdery | 0.05 | 21.12 |
| Kudzu starch | Powdery | 0.05 | 22.71 |

The results show that treating rutin with a naringin-degrading enzyme in the presence of any of the edible components listed-above increases the amount of isoquercitrin produced (yield).

Example 1

Rutin (5 kg) was dispersed in 100 l of water (temperature: 55° C.). To this mixture were added 10 g of naringinase (Amano Enzyme, Inc., trade name: naringinase "Amano", Japan) and each of the edible components (food additives, food ingredients) listed in Tables 1 and 2. The amount of each edible component added was adjusted that to attain the concentration in the mixture prepared as shown in Tables 1 and 2 (0.5 or 0.05 wt. %). The pH of the reaction mixture was 4.7. The reaction solution was left to stand 24 hours at 72° C., and then cooled to 30° C. The components precipitated by cooling were recovered by filtration. Solid filtrates were washed with water and then dried to obtain isoquercitrin.

Example 2

Water (100 l) and corn starch (8 kg) were added to 2 kg of isoquercitrin obtained in Example 1, and the mixture was dispersed uniformly. To this mixture, 2000 ml of CGTase (Amano Enzyme, Inc., trade name: CONTIZYME, Japan) was added, and the mixture was left to stand 26 hours at a temperature of 60° C. and a pH of 7.25. The reaction solution thus obtained was passed through an absorption resin column (Diaion HP-21, manufactured by Mitsubishi Chemical Corporation, Japan) to absorb α-glycosylisoquercitrin. The column was washed with water, and 50 volume % methanol aqueous solution was passed through to desorb. The desorption solution was concentrated and spray-dried to obtain solid matter.

The solid matter thus prepared was subjected to high-performance liquid chromatography (HPLC module manufactured by Jasco Corporation, Column: ODS, Eluant: 25 volume % THF/0.01% phosphoric acid solution), and the constituents thereof were separately collected according to a peak on chromatogram of HPLC. Then, each constituent of the solid matter was analyzed by a mass spectrometry (M-80B, manufactured by Hitachi Ltc., Japan). The results showed that the solid matter was composed of 24 mol % unreacted isoquercitrin and α-glycosylisoquercitrin represented by the formula below:

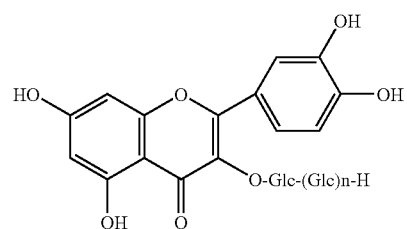

wherein Glc represents a glucose residue, and n represents an integer of 1 or more. Compound wherein n=1:23 mol %, compound wherein n=2:17 mol %, compound wherein n=3:

12 mol %, compound wherein n=4:9 mol %, compound wherein n=5:7 mol %, compound wherein n=6:4 mol %, compound wherein n=7:2 mol %, and compound wherein n=8 or more: 2 mol %.

Example 3

The reaction solution of rutin, naringinase, and edible components obtained in Example 1, were filtered to separate out isoquercitrin. The filtrates removed out isoquercitrin were passed through an absorption resin column (Diaion HP-21, manufactured by Mitsubishi Chemical Corporation, Japan), and filtered through an ultrafiltration membrane with a nominal molecular weight cut-off of 10000. The fraction having a nominal molecular weight of 10000 or less was further introduced to a cation/anion mixed-bed ion exchange resin (manufactured by Organo Corporation). The eluate thus produced was concentrated, dried, and solidified to give rhamnose.

Example 4

Using isoquercitrin obtained in Example 1, an isoquercitrin formulation (liquid) was prepared according to the following prescription.

| Propylene Glycol | 97 (wt. %) |
| Isoquercitrin | 3 |
| Total | 100 wt. % |

Example 5

Using the α-glycosylisoquercitrin mixture (solid) obtained in Example 2, an enzyme-treated isoquercitrin formulation (liquid) was prepared according to the following prescription.

| Propylene Glycol | 90 (wt. %) |
| α-GlycosylIsoquercitrin Mixture | 10 |
| Total | 100 wt. % |

INDUSTRIAL APPLICABILITY

According to the method of the present invention isoquercitrin, which is an intermediate product in the production of α-glycosylisoquercitrin, can be produced in an enhanced yield. Therefore, the present invention is useful not only as a method for efficiently producing isoquercitrin, but also as a method for efficiently producing α-glycosylisoquercitrin. The method is of use as an efficient method for producing α-glycosyl isoquercitrin.

Moreover, as isoquercitrin is produced from rutin, rhamnose is secondarily produced. Hence, from a different perspective, the present invention provides a method for producing rhamnose. The invention is useful as a method capable of producing, from rutin, rhamnose, which is a sugar source, in an enhanced yield.

Furthermore, the isoquercitrin and α-glycosylisoquercitrin formulations can be utilized as antioxidants, anti-fading agents, flavor change inhibitors, and the like in the field of food products, fragrances, cosmetics, etc.

The invention claimed is:

1. A method for producing isoquercitrin comprising the steps of:
   treating rutin with an enzyme having a naringin-degrading activity in the presence of at least one edible component selected from the group consisting of gelatin, wheat gluten, chitosan, lecithin, a glycerol fatty acid ester, xanthan gum, carrageenan, sodium chondroitin sulfate, casein, enzymatically decomposed gelatin, sodium alginate, konjac extract, gellan gum, guar gum, soybean protein, agar, pectin, yeast extract, egg-white peptide, cluster dextrin, gum arabic, arginine, sodium metaphosphate, karaya gum, locust bean gum, sodium pyrophosphate, glucosamine, chitin, sodium glutamate, dextrin, and trehalose, flour, rye, triticale, rice bran, wheat germ, soybean, wheat bran, adzuki bean, barley, foxtail millet, millet, Job's-tears, barnyard millet, corn starch, potato starch, and kudzu starch; and
   obtaining isoquercitrin from the matter treated above.

2. The method for producing isoquercitrin according to claim 1, wherein the glycerol fatty acid ester is at least one member selected from the group consisting of hexaglycerol distearate, tetraglycerol monooleate, tetraglycerol monostearate, decaglycerol monooleate, and decaglycerol stearate.

3. A method for producing rhamnose comprising the steps of:
   treating rutin with an enzyme having a naringin-degrading activity in the presence of at least one edible component selected from the group consisting of gelatin, wheat gluten, chitosan, lecithin, a glycerol fatty acid ester, xanthan gum, carrageenan, sodium chondroitin sulfate, casein, enzymatically decomposed gelatin, sodium alginate, konjac extract, gellan gum, guar gum, soybean protein, agar, pectin, yeast extract, egg-white peptide, cluster dextrin, gum arabic, arginine, sodium metaphosphate, karaya gum, locust bean gum, sodium pyrophosphate, glucosamine, chitin, sodium glutamate, dextrin, and trehalose, flour, rye, triticale, rice bran, wheat germ, soybean, wheat bran, adzuki bean, barley, foxtail millet, millet, Job's-tears, barnyard millet, corn starch, potato starch, and kudzu starch; and
   obtaining rhamnose from the matter treated above.

4. The method for producing rhamnose according to claim 3, wherein the glycerol fatty acid ester is at least one member selected from the group consisting of hexaglycerol distearate, tetraglycerol monooleate, tetraglycerol monostearate, decaglycerol monooleate, and decaglycerol stearate.

5. The method for producing isoquercitrin according to claim 1, wherein the rutin concentration in a reaction mixture that is subjected to an enzyme treatment is 0.1 to 20 wt. %.

6. The method for producing isoquercitrin according to claim 1, wherein the amount of naringin-degrading enzyme in the reaction mixture that is subjected to an enzyme treatment is 0.01 to 5 parts by weight per part by weight of rutin contained in the reaction mixture when the naringin-degrading enzyme has an enzyme-specific activity of about 100 units.

7. The method for producing isoquercitrin according to claim 1, wherein the amount of edible component in the reaction mixture that is subjected to an enzyme treatment is 0.00 1 to 20 parts by weight per part by weight of rutin contained in the reaction mixture.

8. The method for producing isoquercitrin according to claim 1, wherein the enzyme treatment is conducted under the conditions of at about 40° C. to about 75° C., and a pH of about 4 to about 8.

9. The method for producing rhamnose according to claim 3, wherein the rutin concentration in a reaction mixture that is subjected to an enzyme treatment is 0.1 to 20 wt. %.

10. The method for producing rhamnose according to claim 3, wherein the amount of naringin-degrading enzyme in the reaction mixture that is subjected to an enzyme treatment is 0.01 to 5 parts by weight per part by weight of rutin contained in the reaction mixture when the naringin-degrading enzyme has an enzyme-specific activity of about 100 units.

11. The method for producing rhamnose according to claim 3, wherein the amount of edible component in the reaction mixture that is subjected to an enzyme treatment is 0.001 to 20 parts by weight per part by weight of rutin contained in the reaction mixture.

12. The method for producing rhamnose according to claim 3, wherein the enzyme treatment is conducted under the conditions of at about 40° C. to about 75° C., and a pH of about 4 to about 8.

* * * * *